United States Patent [19]

Rose et al.

[11] 4,310,408
[45] Jan. 12, 1982

[54] ELECTROPHORESIS CHAMBER

[75] Inventors: Alan L. Rose; David W. Richman, both of St. Louis, Mo.

[73] Assignee: McDonnell Douglas Corporation, St. Louis, Mo.

[21] Appl. No.: 122,842

[22] Filed: Feb. 20, 1980

[51] Int. Cl.³ ..................... G01N 27/26; G01N 27/40
[52] U.S. Cl. ............................... 204/301; 204/180 R; 204/180 P; 204/299 R
[58] Field of Search .......... 204/180 G, 180 R, 180 S, 204/299 R, 301

[56] References Cited

U.S. PATENT DOCUMENTS

| | | | |
|---|---|---|---|
| 3,412,008 | 11/1968 | Strickler | 204/299 R X |
| 3,450,624 | 6/1969 | Natelson | 204/299 R |
| 3,902,986 | 9/1975 | Nees | 204/180 G X |

Primary Examiner—Arthur C. Prescott
Attorney, Agent, or Firm—Lionel L. Lucchesi

[57] ABSTRACT

A continuous free-flow electrophoresis chamber construction is provided which includes a coolant chamber employing coolant flow in a direction that traverses the flow of buffer carried in a buffer chamber. The construction further employs large area membranes separating first and second electrodes from the buffer flow chamber. The coolant flow chamber communicates with the buffer flow chamber along the membranes.

13 Claims, 5 Drawing Figures

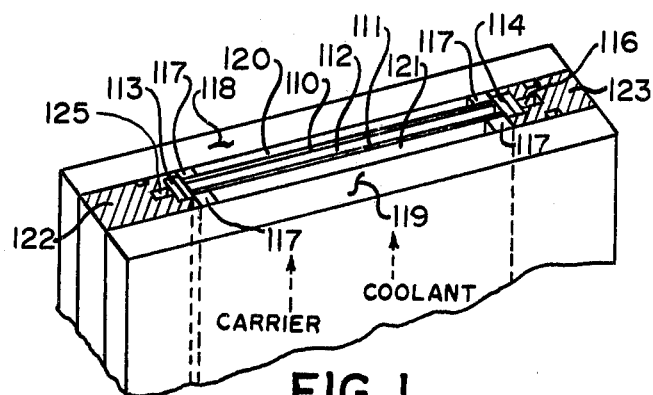
FIG. 1. (PRIOR ART)
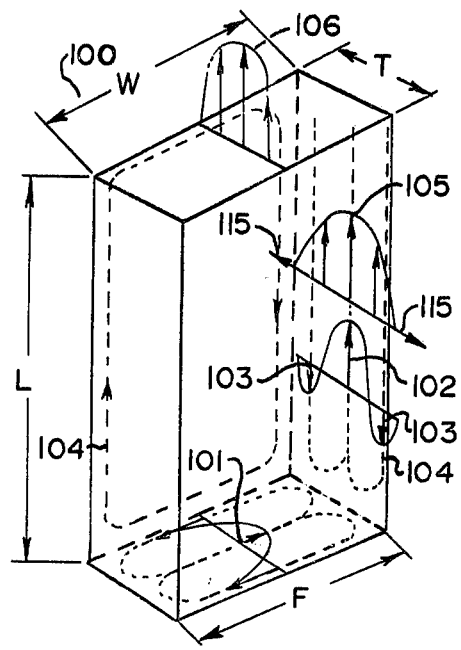
FIG. 2.
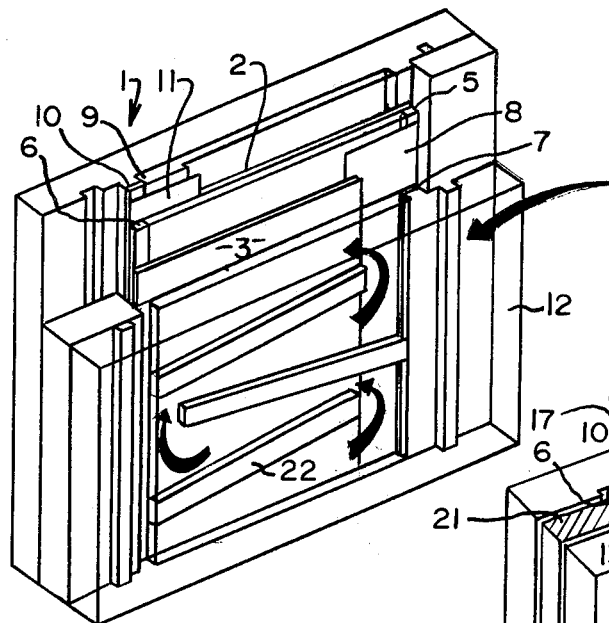
FIG. 3.
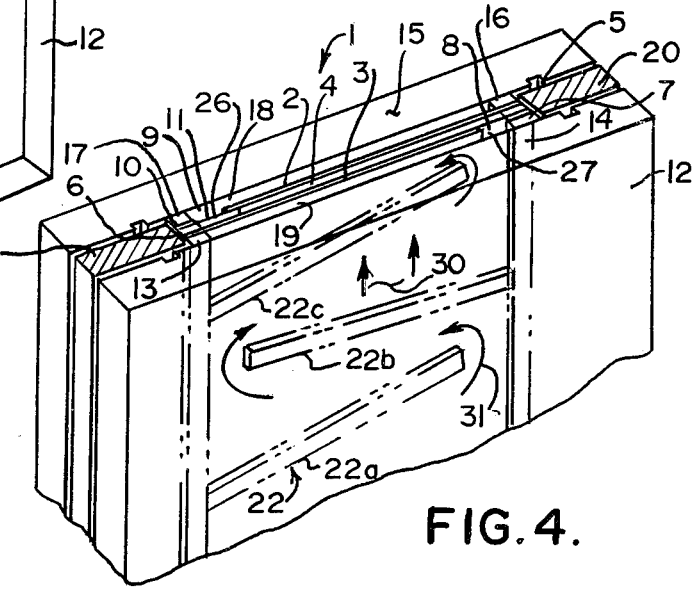
FIG. 4.
PERFORMANCE SUMMARY
|  | OLD | NEW |
|---|---|---|
| HORIZONTAL TEMPERATURE DIFFERENCE STD. DEV. -°C @ 20 VOLTS/CM FIELD STRENGTH | 2.57 | 0.16 |
| RESIDENCE TIME - MINUTES | 25.00 | 48.00 |
| FIELD STRENGTH - VOLTS/CM | 20.00 | 30.00 |
FIG. 5.

ELECTROPHORESIS CHAMBER

BACKGROUND OF THE INVENTION

This invention relates to electrophoresis processes, and in particular, to a construction for an electrophoresis chamber employed in such processes. While the invention is described with reference to a particular electrophoresis process, those skilled in the art will recognize the wider applicability of the inventive principles disclosed hereinafter.

The free-flow electrophoretic process with which the invention disclosed hereinafter finds application is a combination of several phenomenon. As will be appreciated by those skilled in the art, a free-flow electrophoresis process is a continuous laminar flow of a carrier fluid or buffer that flows through a chamber with multiple outlets. A sample stream containing protein, cells, or other particles forms an input into this flow and an electrical field is applied across the flow in the direction of desired separation. The underlying principle for separation is electrical phoresis, that is to say, the motion of charged particles in an electrical field. The applied field results in a force on the particles, which force is proportional to their charge and the electrical field strength. Under the influence of this force, the particles are rapidly accelerated in the direction of the force approaching their terminal velocity for equilibrium with the viscous drag force on the particles. Different particles will, in general, have different lateral velocities and will exit the chamber through different exit ports, accomplishing separation of the sample. The characteristics used to quantify this phenomenon is particle mobility, which is defined for the purpose of this specification in its normal connotation, as the velocity component in the direction of the electrical field divided by the electrical field strength applied to the particle.

If the carrier buffer is a fluid of constant properties, that is to say, constant density and viscosity, the flow can be characterized as Poiseuille flow or fully developed, one dimensional flow between parallel plates. In actual practice, Poiseuille flow is not obtainable. Departures from Poiseuille flow occur near the inlet to the buffer flow chamber and near the sides of the buffer flow chamber, where the membranes used to isolate the electrodes and the surrounding buffer which contains hydrogen and oxygen gas and other possible breakdown products from the buffer flow in the chamber act as a zero velocity boundary. Because the plate spacing defining the buffer flow chamber is small compared to the chamber width, the maximum fluid velocity at the midpoint between the plates is very nearly constant except near the membranes. If the electrical field strength is constant throughout the chamber, then particles forming an input to the carrier buffer will have constant lateral terminal velocities and their paths will be nearly straight lines running diagonally across the chamber length. Carrier buffer conventionally is mostly water with additives to support the viability of the biological materials being separated. Water definitely is not a fluid of constant properties. For terrestrial application of electrophoresis, the important property variation is the variation of density with temperature. Whenever temperature differences exist at the same altitude within the chamber, the less dense fluid experiences an upward buoyant force due to gravity and the more dense fluid experiences a greater downward buoyant force due to gravity. These gravity forces give rise to convection currents that are superimposed on the main flow. In the past, minimizing convection currents in electrophoresis processes has required either that the temperature differences be minimized or that viscous damping of the currents be increased, or both. Chamber thickness as small as 0.6 millimeter has been used in analytical electrophoresis units to provide added viscous damping of convection currents in the flow. Thin chambers, however, result in sample cross sections too small for practical production of pharmaceutical products.

The invention disclosed hereinafter overcomes these prior art difficulties by providing a chamber that combines several structural features to minimize temperature differences in the direction of separation across the buffer flow chamber. In particular, the chamber of this invention employs a cooling flow that traverses the direction of buffer flow to minimize horizontal temperature differences. It also employs a construction in which the cooling fluid and the buffer fluid surrounding the electrodes are one in the same, eliminating temperature differences in the chamber buffer due to temperature differences between cooling fluid and buffer fluid surrounding the electrodes.

One of the objects of this invention is to provide an improved electrophoresis chamber design.

Another object of this invention is to provide an electrophoresis chamber design in which temperature variations in any particular horizontal plane across the chamber are minimized.

Another object of this invention is to provide an electrophoresis chamber design in which temperature differences due to separate cooling fluid and buffer fluid surrounding the electrodes are eliminated.

Another object of this invention is to provide an electrophoresis chamber design in which a serpentine coolant-buffer flow is provided.

Still another object of this invention is to provide an electrophoresis chamber design employing predeterminedly spaced baffles to channel coolant buffer flow in a desired direction.

Other objects of this invention will be apparent to those skilled in the art in light of the following description and accompanying drawings.

SUMMARY OF THE INVENTION

In accordance with this invention, generally stated, an electrophoretic chamber is provided which is constructed so that coolant buffer flow in a coolant buffer chamber is directed transversely to the direction of carrier buffer flow in a buffer flow chamber. First and second electrodes are separated from the buffer flow chamber by respective membranes and chamber walls. The carrier chamber buffer, which is heated by the passage of current due to the electrical field, transfers heat to the coolant buffer along the respective membrane surfaces and chamber walls so as to minimize temperature differences in the carrier chamber buffer. The construction disclosed provides substantial improvement in horizontal temperature deviation in the carrier buffer, permitting longer carrier buffer dwell times and the application of increased field strength, with consequent increased separation during the electrophoretic process.

BRIEF DESCRIPTION OF THE DRAWINGS

In the drawings,

FIG. 1 is a cross sectional view in perspective, partly broken away, of a known construction for a electrophoretic chamber, labelled as prior art;

FIG. 2 is a diagrammatic view of the chamber buffer flows acting on a particle in a electrophoretic process;

FIG. 3 is a view in perspective, partly broken away, of one illustrative embodiment of electrophoretic chamber construction of this invention;

FIG. 4 is a cross sectional view in perspective, partly broken away, of the electrophoretic chamber shown in FIG. 3; and FIG. 5 is a performance comparison between the known electrophoretic chamber shown in FIG. 1 and the electrophoretic chamber of this invention shown in FIG. 3.

DESCRIPTION OF THE PREFERRED EMBODIMENT

Referring now to the drawings, reference numeral 1 indicates one illustrative embodiment of electrophoretic chamber of this invention. In order to fully appreciate the inventive features incorporated in the chamber 1 as later described, reference is first had to FIG. 2, where the chamber buffer flows that affect particle motion are shown.

In FIG. 2, a chamber 100, in diagrammatic illustration, is shown to include a width W, a thickness T, and a length L. An electric field F is applied to the chamber buffer across the width W of the chamber 100, which causes heating of the carrier chamber buffer due to the passage of electrical currents. To limit the increase in temperature of the carrier chamber buffer to acceptable levels, the buffer is cooled by the transfer of heat through the chamber walls as represented by reference numeral 115, illustrating the direction of heat flow. The removal heat from the carrier chamber buffer at the walls in turn causes the temperature to be a maximum at the center plane of the chamber as represented by the reference numeral 105. For water, above the temperature for maximum density, that is 4° C., the force due to gravity is smaller for the less dense fluid near the center plane of the chamber. This force imbalance causes a convective velocity in the upward direction near the center plane of the chamber as indicated by reference numeral 102, and convective velocities in the downward direction near the walls as indicated by reference numeral 103. When these convective velocities become significant relative to the Poiseuille flow velocity profile as indicated by reference numeral 106, unstable flow results. If both the heating caused by the passage of electrical current and the heat removal were uniform across the width of the chamber, horizontal temperature differences would not exist. In practice, however, this is not the case, because the membranes used to isolate the electrodes affect the passage of the current carrying ions causing variation in the electrical resistance of the fluid near the membranes. Where the resistance is greater, the amount of heating is greater and where the resistance is less, the amount of heating is less. This in turn causes higher temperatures where the resistance of the chamber buffer is higher and lower temperatures where the resistance is lower. If the resistance of the chamber buffer is higher near the left membrane and lower near the right membrane, then a convective flow, as indicated by reference numeral 104, results. When these convective velocities become significant relative to the Poiseuille flow velocity as indicated by reference numeral 106, unstable flow results.

The temperature variations in the carrier chamber buffer are the result of the interaction of these flows and yet another flow, called electroosmotic flow. This flow, represented by reference numeral 101, is the result of interaction between the electrical field, the chamber buffer, and charged surface of the chamber walls. This interaction causes a high velocity near the walls and a return flow of chamber buffer near the center plane of the chamber.

A continuous free-flow electrophoresis chamber design known in the prior art is shown in FIG. 1. In this design, a pair of parallel plates 110 and 111 define a carrier buffer chamber 112 therebetween. Again, carrier and particle flow is from the bottom of the carrier buffer chamber 112 toward the top of the carrier buffer 112, directions being referenced to FIG. 1 of the drawings.

A pervious membrane 113 and a pervious membrane 114, with suitable respective support structures, are utilized to close the side edges of the plates 110 and 111. The membranes 113 and 114 segregate the chamber 112 from a first electrode 125 and a second electrode 116, respectively. In operational use, the electrode 125 may be a cathode, while the electrode 116 may be an anode having a predetermined voltage applied between them, so as to exert an electric field across the chamber 112 in a horizontal direction. A plurality of suitable spacers 117 are positioned between the plates 110-111 and a pair of closure members 118 and 119, respectively. In its assembled form, the closure member 118 and the plate 110 define a coolant flow chamber 120 while the plate 111 and closure member 119 defines a coolant flow chamber 121. Suitable supports 122 and 123 are employed to enable the entire structure to be constructed into an integral unit.

In operational practice, the carrier buffer flows from the bottom to the top of the chamber 112, as is indicated by the dashed arrow in FIG. 1. In the design shown, coolant flows over the outboard facing surfaces of the plates 110 and 111 in a direction parallel to the buffer flow, as indicated by the solid arrow shown in FIG. 1. In the design of FIG. 1, coolant flow is separated from the carrier buffer flow by the spacers 117. If the heat dissipation within the carrier buffer is uniform and there is no heat conducted into or out of the membranes 113 and 114 at the ends of the chamber 112, then a uniform parallel cooling flow would be adequate since increase in carrier buffer temperature with length and coolant buffer temperature with length of the chamber 112, would be constant across the chamber. We have found, however, that this is not the case, since the membranes 113 and 114 cause variation in the electrical resistance of the carrier buffer in the vicinity of the membranes. This variation causes non-uniform heat dissipation in the carrier chamber buffer. In addition to the non-uniform heat dissipation, the cooling of the carrier chamber buffer is non-uniform because of the flows of buffer surrounding the electrodes outside the membranes. These flows are required to supply current carrying ions and to carry away the hydrogen and oxygen gas and other possible breakdown products.

The heat transfer problem has an obvious solution and that is to provide the amount of cooling at each location on the walls of the chamber to remove the amount of heat dissipated by the passage of the electrical current. This implies supplying cooling fluid at just the right temperature to cause the proper heat removal to occur at each location on the wall. These conditions are extremely difficult to achieve and control. Their non-control results in the application of the aforementioned forces described in conjunction with FIG. 2, which disturbs particle flow and makes the electrophoresis process unsuitable for the production of commercial quantities of pharmaceuticals, for example.

To overcome the deficiencies associated with known prior art designs, we have developed the chamber 1. In the chamber 1, a pair of plates 2 and 3 define a carrier buffer flow chamber 4, shown in cross lines in FIG. 3. As shown there and in FIG. 4, the edges of the plates 2 and 3 are closed by a support 5 and 6, respectively. A first electrode 7 is placed adjacent a membrane 8, the membrane 8 in turn being supported by plate 3 and a first panel 12. A second electrode 9 is placed adjacent a membrane 11, the membrane 11 in turn being supported by the plate 2 and a second panel 15.

The first panel 12 has a support 13 and a support 14 abutting it so that the support 13 sandwiches the plate 3 between the member 6, while the support 14 sandwiches the electrode 7 and membrane 8 between the member 5.

The second panel 15 has supports 16 and 17 abutting it. The support 17 sandwiches the electrode 9 and the membrane 11 between it and the support 6. The support 16 sandwiches the plate 4 and between it and the member 5 on a second end of the plates 3 and 4. In the assembled relationship shown in FIG. 4, a coolant flow chamber 18 and a coolant flow chamber 19 are positioned on opposite sides of the plates 3 and 4, outboard of those respective plates. A pair of end panels 20 and 21, respectively, support the end structural members of the buffer chamber 1 in the assembled position of the electrophoretic chamber 1.

The coolant flow chambers 18 and 19 each have a plurality of baffle plates 22 mounted in them. The baffles 22 are shown in dashed lines in FIG. 4. Only the flow chamber 19 construction is described in detail, for the sake of simplicity.

In the embodiment shown, a baffle 22a is attached to the support 13, while the next successive baffle 22b is attached to the support 14. The next successive baffle member 22c is again attached to the support 13. As constructed, the baffles extend between the plate 19 and an end wall 23 of the panel 12 on their width dimension, and are either attached to or spaced from the supports 13 and 14 along their length dimension. The baffles thus delimit a serpentine flow path in the coolant flow chamber. The baffles themselves may be constructed from a variety of materials. Original models of the chamber 1 employ plastic baffle members 22a, b, and c, although other materials may be utilized, if desired.

As best observed in FIG. 4, the support plate 2 is spaced from the electrode 9 along an area 26, the electrode 9 being separated from the chamber 4 by the membrane 11. In like manner, the plate 3 is separated from the electrode 7 along an area 27, the electrode 7 being separated from the buffer flow chamber 4 by the membrane 8.

The membranes 8 and 9 are conventional, and in general, any material suitable for use with the particular buffers employed in the chamber 1 may be utilized for the membranes 8 and 9. Those membranes, as indicated above, are pervious to ion flow, and permit the passage of ions between the carrier and coolant employed in the chamber 1. The membranes 8 and 9 are continuous with the chamber walls 3 and 2, allowing heat transfer to the cooling buffer from every location in the chamber buffer. This is an important feature of our invention, in that a continuous cooling chamber equidistant from the chamber buffer eliminates areas of insufficient cooling. Likewise, the baffle members 22 require the coolant flow through the chambers 18 and 19 to traverse the direction of flow of the carrier buffer flow in the chamber 4, traverse being used in its conventional connotation of forcing the flow, as indicated by the numeral 31, across the direction of buffer carrier flow in the chamber 4, that last-mentioned flow being indicated by the flow lines 30 in FIG. 4. As the flow traverses the chamber wall, heat transfer to the coolant buffer is greater where the wall temperature is greater and less where the wall temperature is less, which tends to equalize the wall temperature.

Operation of the chamber 1 is relatively simple to understand. Conventionally, samples for which separation are required are introduced along the bottom of the chamber 1 along the carrier buffer chamber 4. This flow migrates upwardly in the chamber 4 in the direction indicated by the flow lines 30. Coolant fluid is introduced in the chambers 18 and 19 along along the bottom portion of the chamber 1. The buffer coolant flow is forced to traverse the serpentine flow pattern indicated by the flow lines 31 until it reaches the upper end of the chamber 1. Conventionally, the upper end of the chamber 1 is equipped with a plurality of separator tubes which are designed to remove the desired separated sample and the buffer carrier in accordance with conventional electrophoresis theory.

The serpentine flow pattern employed in the buffer flow chambers 18 and 19 have been found to be exceedingly important in maintaining an essentially constant horizontal temperature along a particular altitude level of the plates 2 and 3. In practice, we have found that the convective flow 104 has been largely eliminated with both increased efficiency and increased chamber dwell times. A summary of that performance is shown in FIG. 5, which illustrates that the horizontal temperature difference standard deviation in degrees centigrade decreased from 2.57° C. to 0.16° C. at 20 volts per centimeter field strength. Likewise, the resident time in minutes for successful sample collection increased from 25 minutes to 48 minutes or that the usable field strength increased from 20 volts/cm to 30 volts/cm. The increased dwell time in the chamber means that the chamber 1 is capable of improved separation because temperature variations have been largely eliminated. Likewise, the ability to employ higher field strengths means that the concentration of the product collected through the electrophoretic process is enhanced.

Numerous variations, within the scope of the appended claims, will be apparent to those skilled in the art in light of the foregoing description and accompanying drawings. For example, the design silhouette of the various components employed in the chamber 1 may vary in other embodiments of this invention. Likewise spacing between the plates 2 and 3, and the physical dimensions of the plates can be changed. Various dimensions for parts employed in the chamber design are critical in that the length of the chamber 4 must be chosen so that desired concentrations are obtained at the output side of the device. This is a problem previously addressed in the art, and is not discussed in detail herein. Although various materials were described as used, their disclosure in this specification is not intended to imply that components made of those materials are essential to the successful application of the invention. These variations are merely illustrated.

Having thus described the invention, what is claimed and desired to be secured by Letters Patent is:

1. A chamber for conducting an electrophoretic process, comprising:
   a buffer flow chamber including at least a pair of large surface area plates spaced from and positioned generally parallel to one another to define said buffer flow chamber;
   buffer in said buffer flow chamber flowing in a first direction;
   at least one coolant flow chamber adjacent said buffer flow chamber and in thermal contact therewith;
   coolant buffer in said coolant buffer chamber;
   a first electrode positioned along a first end of said parallel plates;
   a membrane between said electrode and said buffer flow chamber, positioned in the same plane as and continuous with one of said parallel plates;
   a second electrode positioned near a second end of said parallel plates; and
   a second membrane interposed between said second electrode and said buffer flow chamber, positioned in the same plane as and continuous with the other of said parallel plates, said coolant flow chamber and said buffer flow chamber communicating with one another along said first and said second membranes.

2. The chamber of claim 1 further including means in said coolant flow chamber for directing the entire coolant flow therein in a direction generally traversing the axial dimension of said buffer flow chamber.

3. The device of claim 2 wherein said coolant flow is serpentine.

4. The chamber of claim 3 wherein means for directing coolant flow comprises a plurality of baffles arranged in said coolant flow chamber to channel coolant flow in said serpentine direction.

5. A chamber for conducting an electrophoretic process, comprising:
   a buffer flow chamber including at least a pair of plates spaced from one another, said plates defining said buffer flow chamber therebetween;
   buffer in said buffer flow chamber flowing in a first direction;
   an electrode positioned along a first end of said buffer flow chamber;
   a second electrode positioned at a second end of said buffer flow chamber;
   a first membrane between said first electrode and said buffer flow chamber, said first membrane being positioned in the plane of one of said plates so as to be continuous thereof;
   a second membrane positioned between said second electrode and said buffer flow chamber, said first membrane being positioned in the plane of the other of said plates so as to be continuous thereof;
   at least one coolant flow chamber adjacent said buffer flow chamber and in thermal contact therewith;
   coolant in said coolant flow chamber; and
   means in said coolant flow chamber for directing coolant flow therein in a direction generally traversing the direction of buffer flow in said buffer flow chamber, said buffer flow chamber and said coolant flow chamber communicating with one another along said first and said second membranes.

6. The chamber of claim 5 wherein said coolant flow directing means comprises a plurality of baffles arranged in said coolant flow chamber to channel coolant flow in a serpentine direction.

7. The chamber of claim 6 wherein said first and second membranes comprise large areas of pervious devices permitting relatively free ion communication between said coolant flow chamber and said buffer flow chamber.

8. The chamber of claim 7 wherein said baffles comprise a plurality of spaced members abutting one of said plates defining said buffer flow chambers along at least one surface of said baffles.

9. A chamber for conducting an electrophoretic process, comprising:
   a buffer flow chamber including at least a pair of large surface area plates spaced from one another to define said buffer flow chamber;
   buffer in said buffer flow chamber flowing in a first direction;
   at least one coolant flow chamber adjacent said buffer flow chamber and in thermal contact therewith;
   coolant in said coolant flow chamber;
   means in said coolant flow chamber for directing all coolant therein in a direction generally traversing the direction of buffer flow in said buffer flow chamber;
   a first electrode positioned along said first end of said buffer flow chamber;
   a second electrode positioned at a second end of said buffer flow chamber;
   a first membrane interposed between said first electrode and said buffer flow chamber, said first membrane being positioned in the plane of one of the plates forming said plate pair so as to be continuous with said plate; and
   a second membrane interposed between said second electrode and said buffer flow chamber, said buffer flow chamber and said coolant flow chamber communicating with one another along said first and said second membranes, said second membrane being positioned in the plane of the other of the plates forming said plate pair so as to be continuous with said plate.

10. The device of claim 9 wherein said coolant flow is serpentine.

11. The device of claim 10 wherein said means for coolant flow directing comprises a plurality of baffles arranged in said coolant flow chamber to channel coolant from coolant flow in said serpentine direction.

12. A chamber for conducting an electrophoretic process, comprising:
   a buffer flow chamber including at least a pair of plates spaced from one another, said plates defining said buffer flow chamber therebetween;
   buffer in said buffer flow chamber flowing in a first direction;
   a first electrode positioned along a first end of said buffer flow chamber;
   a second electrode positioned along a second end of said buffer flow chamber;
   a first membrane between said first electrode and said buffer flow chamber, said first membrane being positioned in the plane of one of the plates forming said plate pair so as to be continuous with said plate;
   a second membrane between said second electrode and said buffer flow chamber, said second membrane being positioned in the plane of the other of the plates forming said plate pair so as to be continuous with said plate;

at least one coolant flow chamber adjacent said buffer flow chamber and in thermal contact therewith;

coolant in said coolant flow chamber; and means in said coolant flow chamber for directing the entire coolant flow therein in a direction generally traversing the direction of buffer flow in said buffer flow chamber, said buffer flow chamber and said coolant flow chamber communicating with one another along said first and said second membranes, said first and said second membranes being constructed from pervious material permitting relatively free ion communication between said coolant flow chamber and said buffer flow chamber.

13. A chamber for conducting an electrophoretic process, comprising:

a buffer flow chamber including a first large surface area plate, and a second large surface area plate positioned generally parallel with respect to said first plate and being spaced therefrom so as to define said buffer flow chamber;

a first membrane positioned in the plane of said first plate and abutting said plate along an edge thereof so as to form a continuation of said first plate;

a second membrane positioned in the plane of said second plane of said plate and abutting an edge thereof so as to form a continuation of said second plate;

a first electrode positioned in said chamber so that said first membrane is interposed between said first electrode and said buffer flow chamber;

a second electrode positioned in said chamber so that said second membrane is interposed between said second electrode and said buffer flow chamber;

buffer in said buffer flow chamber flowing in a first direction;

at least one coolant flow chamber adjacent said buffer flow chamber and in thermal contact therewith;

coolant in said coolant flow chamber; and means in said coolant flow chamber for directing all coolant therein in a direction generally traversing the direction of buffer flow in said buffer flow chamber, said buffer flow chamber and said coolant flow chamber communicating with one another along said first membrane and said second membrane.

* * * * *